United States Patent
Rauh et al.

(10) Patent No.: US 6,194,215 B1
(45) Date of Patent: *Feb. 27, 2001

(54) METHOD AND DEVICE FOR THE CONTINUOUS MEASUREMENT AND CONTROL OF THE COMPOSITION OF A WETTING-AGENT SOLUTION FOR OFFSET PRINTING

(75) Inventors: Wolfgang Rauh; Stephan Dietzel, both of Munich (DE)

(73) Assignee: Baldwin Grafotec GmbH (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,495
(22) PCT Filed: Feb. 25, 1997
(86) PCT No.: PCT/EP97/00895
  § 371 Date: Aug. 31, 1998
  § 102(e) Date: Aug. 31, 1998
(87) PCT Pub. No.: WO97/32205
  PCT Pub. Date: Sep. 4, 1997

(30) Foreign Application Priority Data
Feb. 29, 1996 (DE) .............................. 196 07 681

(51) Int. Cl.$^7$ .......................... G01N 29/02; G01N 29/18; G01N 35/08
(52) U.S. Cl. .............................. 436/55; 73/597; 422/62; 436/40; 436/50; 436/131; 436/149; 436/150; 436/183
(58) Field of Search ................................. 73/61.49, 597, 73/644; 137/92; 436/39, 40, 50, 52, 55, 131, 149, 150, 183; 422/62

(56) References Cited

U.S. PATENT DOCUMENTS

| | | | |
|---|---|---|---|
| 3,382,706 | 5/1968 | Fitzgerald et al. | ........................ 73/59 |
| 3,954,119 | * 5/1976 | Kunioka et al. | ........................ 137/92 |
| 4,236,406 | * 12/1980 | Reed et al. | ........................ 73/61.1 R |

(List continued on next page.)

FOREIGN PATENT DOCUMENTS

| | | |
|---|---|---|
| 3420794 | 12/1984 | (DE) . |
| 4023977 | 2/1992 | (DE) . |
| 4403344 | 9/1994 | (DE) . |

(List continued on next page.)

OTHER PUBLICATIONS

"Landolt–Bernstein", published by Springer–Verlag, 1997; pp. 99–100–103*.
"Sensonic 10", brochure published by Sensotech GmbH, Germany; pp. 1–6*.
O. Kiyohara et al, Chem. Abstr. 1981, 95, 193201j, Nov. 1981.*
M. I. Davis Chem. Abstr. 1985, 103, 148243x, Nov. 1985.*
G. Douheret et al, Chem. Abstr. 1989, 111, 46055k, Aug. 1989.*
M. I. Davis et al, Chem. Abstr. 1992, 116, 28879f, Jan. 1992.*
G. Douheret et al, J. Chem. Soc. Faraday Trans. 1995, 91, 2291–2298.*

(List continued on next page.)

*Primary Examiner*—Arlen Soderquist
(74) *Attorney, Agent, or Firm*—Ostrolenk, Faber, Gerb & Soffen, LLP

(57) ABSTRACT

The wetting-agent solution proposed contains of water and at least one organic solvent miscible with water. The speed of sound in the solution is measured and, from the value obtained, a control signal is generated to keep the composition of the solution constant.

22 Claims, 2 Drawing Sheets

U.S. PATENT DOCUMENTS

| | | | |
|---|---|---|---|
| 4,608,158 | * 8/1986 | Ghisalberti et al. | 210/96.1 |
| 4,726,221 | * 2/1988 | Tavlarides et al. | 73/61.1 R |
| 4,745,953 | * 5/1988 | Kobayashi et al. | 141/1 |
| 4,916,915 | * 4/1990 | Flinchbaugh | 62/129 |
| 4,934,177 | * 6/1990 | Cuthbertson et al. | 73/32 A |
| 4,971,911 | * 11/1990 | Giles et al. | 436/55 |
| 5,177,975 | * 1/1993 | Mertens | 62/64 |
| 5,255,564 | 10/1993 | Glad et al. | |
| 5,368,817 | * 11/1994 | Sudo et al. | 422/62 |
| 5,473,934 | * 12/1995 | Cobb | 73/61.49 |
| 5,557,047 | * 9/1996 | Koide | 73/597 |
| 5,585,729 | * 12/1996 | Toshima et al. | 324/445 |
| 5,749,295 | * 5/1998 | Kurz | 101/350.1 |
| 5,813,247 | * 9/1998 | Strobl | 62/434 |
| 5,851,837 | * 12/1998 | Stokes et al. | 436/149 |

FOREIGN PATENT DOCUMENTS

| | | |
|---|---|---|
| 4320039 | 12/1994 | (DE) . |
| 0012160 | 6/1980 | (EP) . |
| 0263036 | 4/1988 | (EP) . |
| 0693372 | 1/1996 | (EP) . |
| 55-28022 | * 2/1980 | (JP) . |
| 63-1543 | 1/1988 | (JP) . |
| 3-90359 | 4/1991 | (JP) . |
| 9114177 | 9/1991 | (WO) . |

OTHER PUBLICATIONS

I. S. Forrest Monogr. —Eur. Brew. Conv. 1993, 20, 108–119.*

G. Murer et al. Monogr.—Eur. Brew. Conv. 1993, 20, 120–133.*

P. Hauptmann et al. VDI–Ber. 1992, 939, 121–126.*

W. Burda et al. Tech. Mess. 1993, 60, 376–382.*

I. Iwasa et al. Rev. Sci. Instrum. 1988, 59, 356–361.*

D. Schneditz et al. Kidney Int. 1990, 38, 342–346.*

I. S. Forrest Chem. Abstr. 1995, 122, #8244r.*

* cited by examiner

METHOD AND DEVICE FOR THE CONTINUOUS MEASUREMENT AND CONTROL OF THE COMPOSITION OF A WETTING-AGENT SOLUTION FOR OFFSET PRINTING

The invention relates to a method and a device for continuously measuring and regulating the composition of a dampening medium solution for offset printing, the said solution consisting of water and of at least one organic solvent miscible with water, such as, in particular, short-chain alcohols, glycols or glycol ethers.

In the offset printing method, the printing form consists of a thin metal plate which is covered with a photosensitive layer. This layer may be hardened according to the particular image, so that a flat printing form is obtained. The printing and nonprinting parts lie virtually in one plane and differ only in their wetting capacity. The nonprinting hydrophilic regions can be wetted particularly well with water or a mixture of water and water-soluble organic solvents, the dampening medium solution, and very poorly with oily fluids. Preferably, 2-propanol is used as the main organic component in these dampening medium solutions in concentrations of between 3 and 15 percent by volume.

During the printing operation, the dampening medium solution is transported out of a dampening unit as a thin liquid film onto the printing plate. The nonprinting regions of the printing form take up some of the dampening medium solution there, whereas, on the oleophilic printing regions of the printing form, the dampening medium solution is repelled and therefore remains on the dampening applicator rollers and, in the dampening medium fountain of the printing machine, is mixed again with the dampening medium solution located there.

The dampening medium solution therefore has to be constantly supplemented by an amount corresponding to the quantity taken up by the printing plate. This supplementing of the volume is carried out, by means of a dampening medium treatment system. In this system, the dampening medium solution is cooled, supplemented in its volume and recirculated again to the dampening medium fountain. In addition, this system has the task of supplementing the fraction of 2-propanol in the dampening medium solution, the content of 2-propanol decreasing during the continuously running printing operation on account of its rate of evaporation being markedly higher than that of water. The metering of 2-propanol during the treatment of the dampening medium solution is usually controlled by checking the density of the dampening medium solution and by a metering means connected to the density checking means. A system of this kind is known, for example, from DE-A 41 36 263.

Controlling the composition of the dampening medium solution by means of a density check leads, in practice, to pronounced differences between the measured or regulated value and the actual content in the solution. Deviations of 50% or greater are not exceptional. The reason for this is the slight variation in the absolute density values in the concentration range which is relevant for practical use. Moreover, falsifications of the readings due to dirt on the buoyancy bodies cannot be entirely ruled out. Tests to minimize this problem by enlarging the buoyancy bodies have led to an improvement, but have not been able to compensate the basic weaknesses of the method. Density variations basically remain highly susceptible to the infiltration of salt from the additives and papers used and to temperature fluctuations. These influences are, known and have been accepted in the past. In the case of a 2-propanol content of 12 to 15%, they have constituted a high, but nevertheless acceptable measured value deviation.

Printing studies in recent years have shown, however, that it is possible, without restricting production reliability, to print with a 2-propanol content of 7–8%. Specially designed dampening units in combination with optimized additives have made it possible even to use markedly lower 2-propanol contents. In these concentration ranges, the basically unavoidable measured value deviations in the density check are no longer acceptable.

Alternatively to the density check, a series of other techniques are described, which make it possible to check the 2-propanol content. Such known methods are, for example, the measurements of refractive index, viscosity and conductivity. Moreover, EP-A-0,159,412 describes measuring the surface tension in order to determine the 2-propanol content. Another technique for accurately determining the 2-propanol content is spectral absorption, such as is known, for example, from DE-A-43 24 141. In DE-A-43 40 026, the measurement of the concentration of 2-propanol is carried out in the gas phase.

None of these methods has proved successful in practical uses. In some cases, the corresponding sensor technology was not sufficiently robust in light of the soiling occurring in practice. In other cases, the production of the sensors and of the associated control units incurred costs which were too high.

The object on which the invention is based is, therefore, to specify a method and a device, as a result of which particularly accurate measurement and regulation of the composition of dampening medium solutions for offset printing are ensured.

This object is achieved by means of the features of the various embodiments of the present invention.

According to the invention, the sound propagation velocity in the dampening medium solution is measured and a regulating signal is formed from this, in order to keep the composition of the dampening medium solution constant.

The tests on which the invention is based showed that measuring the sound velocity makes it possible to detect changes in concentration of less than 0.1% with reproducible way. Moreover, the percentage change in the measurement signal when the sound velocity is measured is higher by a multiple of that obtained using density measurement.

Furthermore, the method according to the invention has markedly lower dependence on a change in concentration due to salts from the untreated water or from paper constituents. Further advantages and embodiments of the invention are explained in more detail with reference to the following description and the drawing in which.

Figure 1:
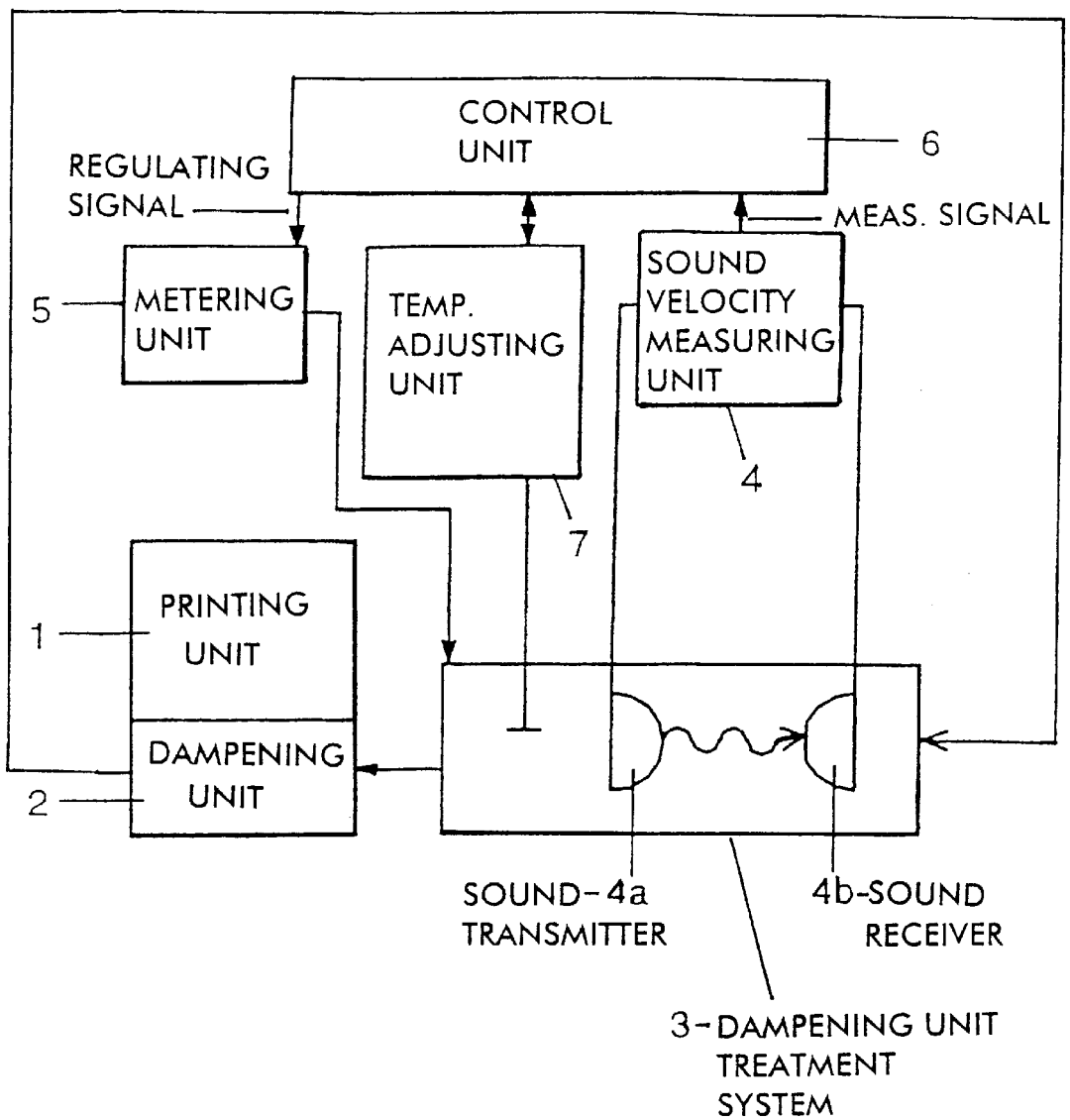
FIG. 1 shows a diagrammatic illustration of a device for offset printing.

The offset printing device illustrated diagrammatically in FIG. 1 consists essentially of a printing unit 1, a dampening unit 2 and a dampening medium treatment system 3.

Furthermore, a means for measuring the sound velocity of the dampening medium solution located in the dampening medium treatment system is provided. Said means is designed, for example, as an immersion probe which has a sound transmitter 4a, in particular an ultrasonic transmitter, and a sound receiver 4b. Another possibility is to design the means for measuring the sound velocity as a tubular probe and arrange it, for example, in the connecting line between the dampening unit 2 and the dampening medium treatment system 3.

Furthermore, the dampening medium treatment system 3 is connected to a metering unit 5, by means of which the addition of an organic solvent miscible with water to the dampening medium solution can be adjusted. Moreover, a control unit 6 is provided, in which the measurement signal determined by the means 4 for measuring the sound velocity is converted into a regulating signal which controls the metering of the solvent from the metering unit 5 in such a way that the composition of the dampening medium is kept essentially constant.

The temperature of the dampening medium solution in the dampening medium treatment system 3 is measured and, if appropriate, readjusted via a means 7.

During a printing operation, the dampening medium solution is transported out of the dampening unit 2 onto a printing plate of the printing unit 1. The nonprinting regions of the printing plate take up some of the dampening medium solution there, whereas, on the oleophilic printing regions of the printing plate, the dampening medium solution is repelled and, in a dampening medium fountain of the dampening unit 2, is mixed again with the dampening medium solution located there. Used or depleted volume of the dampening medium solution is supplemented in the dampening medium treatment system 3. In this system, the dampening medium solution is cooled via the means 7, supplemented in its volume and recirculated again to the dampening unit 2.

The dampening medium solution consists of water and of at least one organic solvent miscible with water, such as, in particular, short-chain alcohols, glycols or glycol ethers. Furthermore, various additives are added to the dampening medium solution. 2-propanol is preferably used as the solvent, its content decreasing in the dampening medium solution during the continuously running printing operation on account of its rate of evaporation being markedly higher than that of water. In the method according to the invention, in order to control the metering of the solvent, the sound propagation velocity in the dampening medium solution is determined. For this purpose, the sound transmitter 4a emits a brief signal which is propagated in the dampening medium solution and is picked up by the sound receiver 4b. If the distance between the transmitter and receiver is constant, the sound velocity can be calculated directly by measuring the time required by the sound signal between the transmitter and receiver. Every liquid has a specific propagation velocity for sound waves. In a liquid mixture consisting, for example, of two components, the fractions of the two components can therefore be calculated by measuring the sound velocity.

According to the invention, this measurement principle, which is known per se, is also used to determine the concentration of the solvent in the dampening medium solution for offset printing. Tests on which the invention is based showed, however, that the measurement signal can be falsified by small gas bubbles located in the dampening medium solution and, as a result, the measurement of sound velocity is subject to pronounced fluctuations. It is therefore necessary to provide means which prevent the formation of a regulating signal which is based on a sound propagation velocity measurement which is faulty due to gas bubbles in the dampening medium solution.

This could be implemented, for example, by means of a degassing chamber, such as is known from the prior art. Another possibility is for those measurement signals falsified by gas bubbles to be ignored when the regulating signal is formed. This may be carried out, in particular, by means of suitable software in the control unit 6. It proves particularly advantageous in this respect that the measurement signals falsified by gas bubbles differ markedly from the proper measurement signals. The control unit 6 then forms, as a function of the measured sound velocity, a regulating signal by means of which the content of the solvent may, if appropriate, be varied via the metering unit 5.

Since the sound propagation velocity of a solution depends very closely on temperature, moreover, the temperature is determined by the means 7. The dampening medium solution is normally maintained at a specific temperature. There is also the possibility, however, of taking the temperature into account when the regulating signal is formed.

Insofar as the dampening medium solution contains a plurality of solvents, a corresponding number of metering units 5 may also be provided.

By means of this method, the composition of the dampening medium solution, and therefore, in particular, the concentration of the solvent, can be kept constant.

In addition to the metering unit 5 for the solvent or solvents, further adding means are, of course, also provided, though not being illustrated in the drawing, in order to supplement the further constituents of the dampening medium solution, such as, in particular, water and various additives.

EXAMPLE 1

In order to calibrate a dampening medium treatment system, test mixtures of deionized water with an increasing content of 2-propanol were produced. At 25° C., these mixtures gave the following sound velocities and densities:

| 2-Propanol content [%] | Sound velocity [m/s] | Density [g/cm$^3$] |
| --- | --- | --- |
| 0 | 1494.2 | 0.995 |
| 3 | 1517.0 | 0.993 |
| 6 | 1537.0 | 0.989 |
| 12 | 1577.9 | 0.980 |

Figure 2:
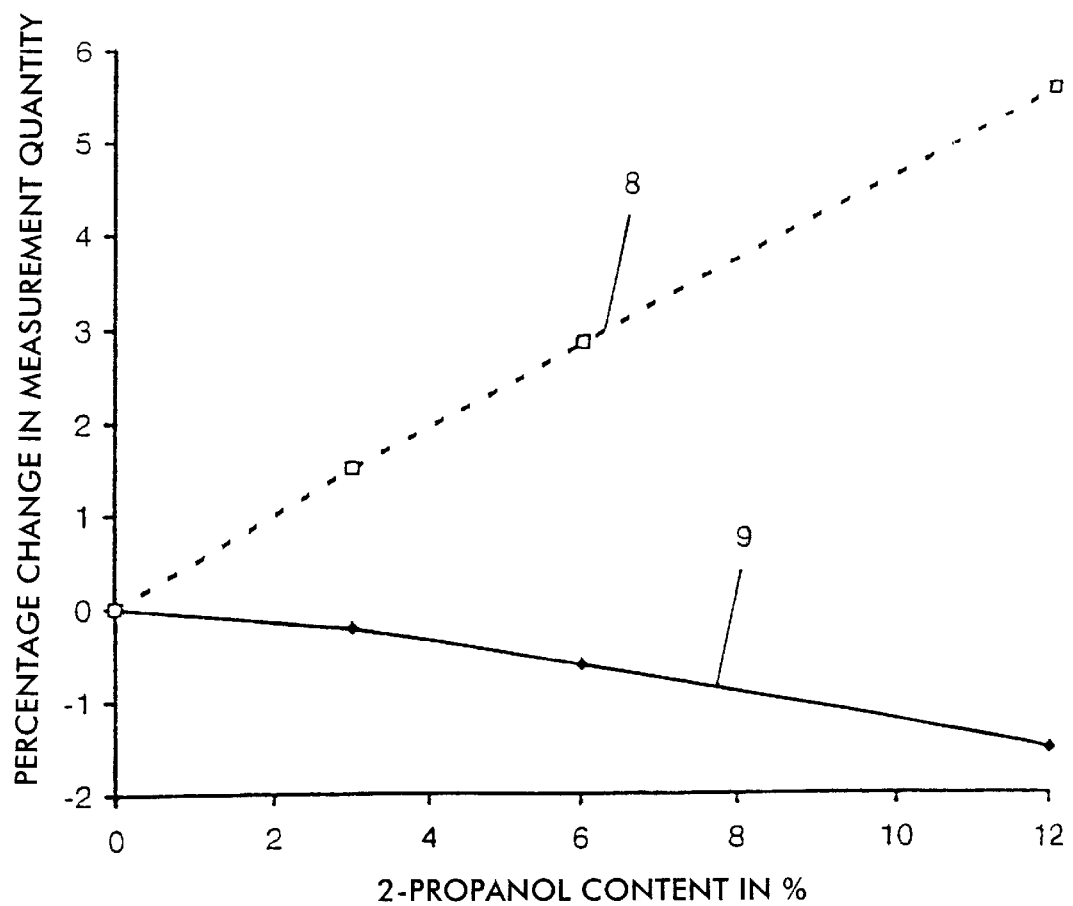
FIG. 2 shows a graph of the percentage change in the measurement quantity in relation to the solvent content.

In the graph of FIG. 2, the percentage change in the measurement quantity of Example 1 is plotted as a percentage against the 2-propanol content. The broken line 8 corresponds, in this case, to the values determined in the sound velocity measurement, while the unbroken line 9 is attributable to the density measurement.

The percentage change in the measurement quantity over the measured range during the measurement of the sound velocity is 5.6%, as compared with 1.51% in the density measurement. The ultrasonic measurement thus leads to a substantially greater percentage change in the measurement quantity and therefore makes it possible to determine the concentration of the solvent in the dampening medium solution with correspondingly greater accuracy.

The sound velocity can be measured to an accuracy of ±0.1 m/s, insofar as a sufficiently accurate temperature measurement of ±0.1° C. can be ensured. In the case of a sound velocity of about 1500 to 1650 m/s in a 2-propanol/water mixture, this allows a reliable measurement of changes in concentration of less than 0.1%.

EXAMPLE 2

Mixing the test mixtures from Example 1 with 2% sodium chloride, this quantity being far removed from the salt concentrations found in practice, gives the following sound velocities and densities at 25° C.:

| 2-Propanol content [%] | Sound velocity [m/s] | Density [g/cm$^3$] |
|---|---|---|
| 0 | 1520.4 | 1.013 |
| 3 | 1538.6 | 1.007 |
| 6 | 1558.1 | 1.005 |
| 12 | 1597.2 | 0.995 |

If the measured values of these highly salted solutions are compared with the calibration curves, it is shown that, when the sound velocities are considered, an average deviation corresponding to an approximately 3% higher 2-propanol content is indicated. When the deviations in the density values are considered, the density values, are higher than those in Example 1 and result in a shift of the measured values into a range which is no longer covered by the measuring spindles conventional in practice, which are generally designed for density measurements in the range of 0.995 to 0.96 g/cm$^3$.

The measurement signal on the ultrasonic principle therefore has markedly lower dependence on a change in concentration due to salts from untreated water or from paper constituents.

EXAMPLE 3

Measuring the sound velocity on a dampening medium mixture extracted from an offset printing machine during continuous production gave a value of 1619.5 m/s. According to the calibration curve, this value corresponds to a 2-propanol content of 17.9%.

The density of the dampening medium was determined at 0.984 g/cm$^3$. According to the calibration curve, this density value corresponds to a 2-propanol content of 9.3%.

When these two measured values from the percentage check are compared with a gas-chromatographic calibration value of 17.4% determined in the laboratory, the superiority of the method according to the invention using sound velocity measurement is revealed here, too.

The method according to the invention makes it possible not only to detect and regulate the 2-propanol content of aqueous dampening medium solutions, but also to check dampening medium solutions which are composed of other organic substances.

What is claimed is:

1. A method for continuously measuring and regulating the composition of a dampening medium solution that is used for offset printing, wherein the solution is comprised of water and at least one organic solvent that is miscible with water wherein at least one of said organic solvent consists of 2-propanol, short-chain alcohols, glycols, glycol ethers or mixtures of these substance groups, the method comprising:
    measuring the sound propagation velocity in the dampening medium solution;
    producing a regulating signal corresponding to the velocity of sound in the solution; and
    keeping the composition of the dampening medium solution constant based upon the velocity measurement.

2. The method of claim 1, further comprising measuring the temperature of the dampening medium solution.

3. The method of claim 2, further comprising taking the measured temperature into account when producing the regulating signal for keeping the composition of the solution constant.

4. The method of claim 1, further comprising maintaining the dampening medium solution at a pre-determined temperature.

5. The method of claim 1, further comprising preventing the formation of a regulating signal based on the measurement of sound propagation velocity if the measurement is faulty due to the presence of gas bubbles at least in the vicinity of where velocity is measured.

6. The method of claim 5, further comprising removing gas bubbles from the region of where sound velocity is being measured.

7. The method of claim 5, further comprising not taking into account faulty measurements of sound velocity which are caused by gas bubbles when the regulating signal is being produced.

8. The method of claim 1, further comprising using the regulating signal for keeping the composition of the solution constant by metering solvent to the solution.

9. The method of claim 1, wherein 2-propanol is used as an organic solvent in the medium.

10. The method of claim 1, wherein short-chain alcohols, glycols or glycol ethers or mixtures of any of these are used as an organic solvent in the solution.

11. A dampening medium treatment system in an offset printing device for continuously measuring and regulating the composition of a dampening medium solution, the dampening medium solution consisting of water and of at least one organic solvent miscible with water, wherein at least one of said organic solvents consists of 2-propanol, short-chain alcohols, glycols, glycol ethers or mixtures of these substance groups, and the system comprising:
    means for measuring the sound velocity in the dampening medium solution;
    means for providing a regulating signal as a function of the measured sound velocity; and
    metering means for metering solvent into the medium solution for maintaining the composition of the solution constant as a function of the regulating signal.

12. The dampening medium treatment system of claim 11, further comprising means for avoiding faulty measurements of the sound velocity caused by gas bubbles when the means for providing the regulating signal is operating to provide that signal.

13. The dampening medium treatment system according to claim 11, wherein the dampening medium solution includes an organic solvent which is miscible with water.

14. An offset printing device, comprising:
    a printing unit;
    a dampening unit for supplying a dampening medium solution to the printing unit; and
    a dampening medium treatment system including a sound transmitter and a sound receiver for measuring the sound velocity of the dampening medium solution, the dampening medium solution consisting of water and of at least one organic solvent miscible with water, wherein at least one of said organic solvent consists of 2-propanol, short-chain alcohols, glycols, glycol ethers or mixtures of these substance groups.

15. The offset printing device according to claim 14, further comprising a metering unit by which solvent can be delivered to the dampening medium solution in response to the measured sound velocity of the dampening medium solution.

16. The offset printing device according to claim 14, further comprising a temperature adjuster for maintaining the temperature of the dampening medium solution at a predetermined temperature.

17. The offset printing device according to claim 14, further comprising a control unit for converting a measurement signal representing the measured sound velocity into a regulating signal to control the metering unit to deliver solvent so as to maintain the composition of the dampening medium solution at a constant level.

18. The offset printing device according to claim 17, further comprising a temperature measuring element for measuring the temperature of the dampening medium solution, wherein the control unit takes into account the measured temperature of the dampening medium solution in the formation of the regulating signal.

19. The offset printing device according to claim 17, further comprising a degassing chamber for preventing the formation of the regulating signal based on a faulty sound velocity measurement due to the presence of gas bubbles in the dampening medium solution.

20. The offset printing device according to claim 14, wherein the sound transmitter is an ultrasonic transmitter provided in an immersion probe.

21. The offset printing device according to claim 14, further comprising a dampening medium solution contained in the dampening unit.

22. The offset printing device according to claim 21, wherein the dampening medium solution includes an organic solvent which is miscible with water.

* * * * *